United States Patent
Hu et al.

(10) Patent No.: US 6,646,166 B1
(45) Date of Patent: Nov. 11, 2003

(54) PROCESSES FOR THE PREPARATION OF 1,4-DIARYL-2-FLUORO-1,3-BUTADIENE AND 1,4-DIARYL-2-FLUORO 2 BUTENE COMPOUNDS

(75) Inventors: Yulin Hu, Plainsboro, NJ (US); David Allen Hunt, Clifton Park, NY (US); Keith Douglas Barnes, Newtown, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,927

(22) PCT Filed: Sep. 11, 1999

(86) PCT No.: PCT/US99/26387
§ 371 (c)(1),
(2), (4) Date: Oct. 1, 2001

(87) PCT Pub. No.: WO00/29363
PCT Pub. Date: May 25, 2000

Related U.S. Application Data

(63) Continuation-in-part of application No. 09/192,682, filed on Nov. 16, 1998, now abandoned.

(51) Int. Cl.[7] ......................... C07C 43/263; C07C 43/29
(52) U.S. Cl. ..................... 568/610; 568/309; 570/129
(58) Field of Search .................. 570/123, 124, 570/127, 128, 129; 568/303, 308, 309, 322, 323, 579, 607, 608, 609, 610

(56) References Cited

U.S. PATENT DOCUMENTS

| | | | | |
|---|---|---|---|---|
| 4,273,787 A | * | 6/1981 | Galantay | 514/679 |
| 5,880,162 A | * | 3/1999 | Khambay et al. | 514/683 |
| 5,892,131 A | * | 4/1999 | Barnes et al. | 568/639 |
| 6,207,846 B1 | * | 3/2001 | Barnes et al. | 556/447 |
| 6,342,642 B1 | * | 1/2002 | Hu et al. | 568/637 |

FOREIGN PATENT DOCUMENTS

| | | | |
|---|---|---|---|
| EP | 811 593 | * | 5/1997 |
| EP | 0811593 A | | 12/1997 |

OTHER PUBLICATIONS

S. Hibi, J. of Medical Chemistry, vol. 41, No. 17, Aug. 13, 1998, pp. 3245–3252.
D. H. Wadsworth, J. Organic Chemistry, vol. 30, No. 3, Mar. 12, 1965, pp. 680–685.
S. Kagabu, J. Chemical Society, Chemical Communications, No. 6, Mar. 15, 1991, pp. 408–410.

* cited by examiner

Primary Examiner—Jean F. Vollano
(74) Attorney, Agent, or Firm—Keil & Weinkauf

(57) ABSTRACT

The present invention provides an improved process for the preparation of 1,4-diaryl-2-fluoro-1,3-butadiene compounds of the structural formula I

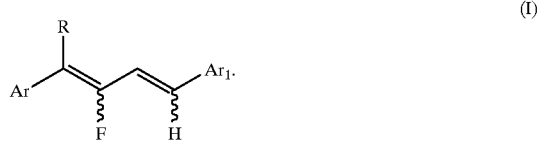

(I)

In addition, the present invention provides an improved process for the preparation of 1,4-diaryl-2-fluoro-2-butadiene compounds of the structural formula IV

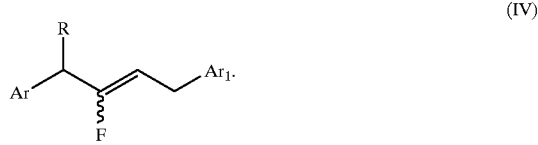

(IV)

15 Claims, No Drawings

PROCESSES FOR THE PREPARATION OF 1,4-DIARYL-2-FLUORO-1,3-BUTADIENE AND 1,4-DIARYL-2-FLUORO 2 BUTENE COMPOUNDS

This application is a 371 of PCT/US99/26387, filed Nov. 9, 1999, now WO 00/29363, which is a CIP of US 09/192,687 filed Nov. 5 1998, now abandoned.

BACKGROUND OF THE INVENTION 1,4-Diaryl-2-fluoro-1,3-butadiene compounds, methods for their preparation, and their use as intermediates in the preparation of 1,4-diaryl-2-fluoro-2-butene insecticidal and acaricidal agents are described in EP 811593-A1. The methods described in EP 811593-A1 for the preparation of 1,4-diaryl-2-fluoro-1,3-butadiene compounds require the use of phosphonium halide compounds. However, these methods are not entirely satisfactory because the required phosphonium halide compounds are relatively expensive and produce undesirable by-products which are difficult to remove from the 1,4-diaryl-2-fluoro-1,3-butadiene compounds. Accordingly, a need exists in the art for an improved process for the preparation of 1,4-diaryl-2-fluoro-1,3-butadiene compounds which avoids the use of phosphonium halide compounds.

It is, therefore, an object of the present invention to provide an improved process for the preparation of 1,4-diaryl-2-fluoro-1,3-butadiene compounds which avoids the use of phosphonium halide compounds.

It is also an object of the present invention to provide an improved process for the preparation of 1,4-diaryl-2-fluoro-2-butene compounds.

Other objects and advantages of the present invention will be apparent to those skilled in the art from the description below and the appended claims.

SUMMARY OF THE INVENTION

The present invention provides a new process for the preparation of 1,4-diaryl-2-fluoro-1,3-butadiene compounds of the structural formula I

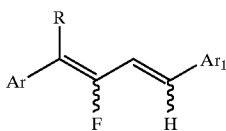

(I)

wherein
R is $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
phenyl optionally substituted with any combination of from one to five halogen, $C_1$–$C_4$alkyl, $C_1$–$C_4$haloalkyl, $C_1$–$C_4$alkoxy, or $C_1$–$C_4$haloalkoxy groups,
biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
which process comprises reacting an arylmethanesulfonyl fluoride or arylmethanephosphonate compound of the structural formula II $$Ar_1CH_2Y \qquad (II)$$

wherein Y is $SO_2F$ or $P(O)(OR_1)_2$, $R_1$ is $C_1$–$C_4$alkyl, and $Ar_1$ is as hereinbefore defined with a 3-aryl-2-fluoropropenal compound of the structural formula III

(III)

wherein R and Ar are as hereinbefore defined in the presence of a base.

The present invention further provides a new process for the preparation of 1,4-diaryl-2-fluoro-2-butene compounds of the structural formula IV

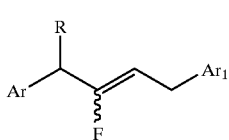

(IV)

wherein
R is $C_1$–$C_4$alkyl, $C_1$–$C_4$haloalkyl, $C_3$–$C_6$cycloalkyl or $C_3$–$C_4$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy, or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, which process comprises the steps of:

(a) reacting an arylmethanesulfonyl fluoride or arylmethanephosphonate compound of the structural formula II

wherein Y is $SO_2F$ or $P(O)(OR_1)_2$, $R_1$ is $C_1$–$C_4$alkyl, and $Ar_1$ is as described above with a 3-aryl-2-fluoropropenal compound of the structural formula III

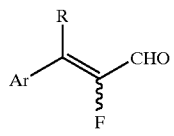

wherein R and Ar are as described above in the presence of a base to form a 1,4-diaryl-2-fluoro-1,3-butadiene compound of the structural formula I

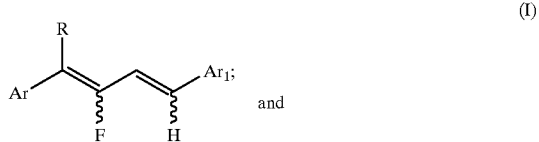

(b) reacting the 1,4-diaryl-2-fluoro-1,3-butadiene compound with: (1) an alkaline earth metal in the presence of a protic solvent, or (2) an alkali metal in the presence of an aprotic solvent.

DETAILED DESCRIPTION OF THE INVENTION

In a preferred embodiment of the present invention, the 1,4-diaryl-2-fluoro-1,3-butadiene compounds of formula I are prepared by reacting an arylmethanesulfonyl fluoride or arylmethanephosphonate compound of formula II with a 3-aryl-2-fluoropropenal compound of formula III and a base, preferably at a temperature ranging from about −78° C. to 150° C., more preferably from about −20° C. to about 100° C., in the presence of a solvent.

In another preferred embodiment of the present invention, the 1,4-diaryl-2-fluoro-2-butene compounds of formula IV are prepared by reacting an arylmethanesulfonyl fluoride or arylmethanephosphonate compound of formula II with a 3-aryl-2-fluoropropenal compound of formula III and a base, preferably at a temperature ranging from about −78° C. to about 150° C., more preferably from about −20° C. to about 100° C., in the presence of a solvent to form a 1,4-diaryl-2-fluoro-1,3-butadiene compound of formula I, and reacting the formula I butadiene compound with an alkaline earth metal in the presence of a protic solvent.

Most advantageously, the present invention provides a process for the preparation of 1,4-diaryl-2-fluoro-1,3-butadiene compounds which avoids the use of phosphonium halide compounds.

The product formula I and IV compounds may be isolated by diluting the reaction mixture with water and extracting the product with a suitable extraction solvent. In the isolation procedure, conventional extraction solvents such as diethyl ether, ethyl acetate, toluene, methylene chloride, and the like, and mixtures thereof may be utilized.

Bases suitable for use in the present invention include, but are not limited to, alkali metal hydrides such as sodium hydride and the like; alkali metal $C_1$–$C_6$alkoxides such as sodium methoxide and the like; alkali metal hydroxides such as potassium hydroxide, sodium hydroxide and the like; alkali metal carbonates such as potassium carbonate, sodium carbonate and the like; alkaline earth metal hydroxides such as calcium hydroxide and the like; alkaline earth metal carbonates such as calcium carbonate and the like; lithium bases such as alkyllithiums including n-butyllithium, sec-butyllithium, tert-butyllithium, methyllithium and the like, lithium dialkylamides including lithium diiso-propylamide and the like, and lithium cyclicamides including lithium tetramethylpiperidine and the like; and tri($C_1$–$C_6$alkyl) amines such as trimethylamine, triethylamine, tripropylamine, tributylamine, diisopropylethylamine and the like. Preferred bases include alkali metal $C_1$–$C_6$alkoxides and alkali metal carbonates.

Solvents useful in the preparation of the formula I compounds of this invention include, but are not limited to, carboxylic acid amides such as N,N-dimethylformamide, N,N-dimethylacetamide and the like; ethers such as diethyl ether, tetrahydrofuran, dioxane, 1,2-dimethoxyethane and the like; nitrites such as acetonitrile, propionitrile and the like; dialkyl sulfoxides such as dimethyl sulfoxide and the like; aromatic hydrocarbons such as toluene, benzene, xylenes, mesitylene and the like; and $C_1$–$C_6$alcohols such as methanol, ethanol, isopropanol, propanol and the like; and mixtures thereof. Preferred solvents includes ethers and nitriles.

Protic solvents suitable for use in this invention include, but are not limited to, $C_1$–$C_6$alcohols such as methanol, ethanol and the like. Preferred protic solvents include methanol and ethanol.

Aprotic solvents include, but are not limited to, ammonia; and ethers such as diethyl ether, tetrahydrofuran, dioxane, 1,2-dimethoxyethane and the like.

Alkaline earth metals suitable for use in the preparation of the formula IV compounds include, but are not limited to, magnesium and calcium with magnesium being preferred. Alkali metals include, but are not limited to, lithium, sodium and potassium.

In another preferred embodiment of the present invention, the arylmethanesulfonyl fluoride or arylmethanephosphonate compound is reacted with the 3-aryl-2-fluoropropenal compound and the base in the presence of a catalytically effective amount of a phase transfer catalyst. Phase transfer catalysts suitable for use in this invention include, but are not limited to, crown ethers such as 18-crown-6, 15-crown-5, 12-crown-4 and the like; quaternary ammonium salts such as tricaprylymethylammonium chloride and the like; and cryptands such as 1,4,10-trioxa-7,13-diazacyclopentadecane, 4,7,13,18-tetraoxa-1,10-diazabicyclo-[8.5.5]eicosane, 4,7,13,16,21,24-hexaoxa-1,10-diazabicyclo[8.8.8]hexacosane, 5,6-benzo-4,7,13,16,21,24-hexaoxa-1,10-diazabicyclo[8.8.8]hexacosane and the like.

In a preferred process of this invention, $R_1$ is an ethyl group when an arylmethanephosphonate compound is used to prepare the formula I compounds.

Preferred formula I and II compounds which may be prepared by the processes of this invention are those wherein
R is $C_1$–$C_4$alkyl, $C_1$–$C_4$haloalkyl, $C_3$–$C_6$cycloalkyl or $C_3$–$C_6$halocycloalkyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
   3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
   3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

Highly preferred 1,4-diaryl-2-fluoro-1,3-butadiene and 1,4-diaryl-2-fluoro-2-butene compounds which may be prepared by the processes of this invention are those wherein
R is isopropyl or cyclopropyl;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

The present invention is especially useful for the preparation of
   1-(p-chlorophenyl)-1-cyclopropyl-2-fluoro-4-(4-fluoro-3-phenoxyphenyl)-1,3-butadiene; and
   1-[1-(p-chlorophenyl)-2-fluoro-4-(4-fluoro-3-phenoxyphenyl)-2-butenyl]cyclopropane.

In formulas I and IV above, the 5- and 6-membered heteroaromatic ring may suitably be a ring containing one to four heteroatoms selected from N, O and S, wherein the heteroatoms may be the same or different, e.g. the rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted a as described in formulas I and IV above.

Exemplary of "halogen" as used herein are fluorine, chlorine, bromine and iodine. The terms "$C_1$–$C_4$haloalkyl", "$C_3$–$C_6$halocycloalkyl" and "$C_1$–$C_4$haloalkoxy" are defined as a $C_1$–$C_4$alkyl group, a $C_3$–$C_6$cycloalkyl group and a $C_1$–$C_4$alkoxy group substituted with one or more halogen atoms, respectively, wherein the halogen atoms may be the same or different.

When used herein as a group or part of a group the term "alkyl" includes straight or branched chain alkyl groups such as methyl, ethyl, n-propyl, isopropyl, n-butyl, isobutyl, s-butyl and t-butyl. When used herein as a group or part of a group the term "cycloalkyl" incudes cyclopropyl, cyclobutyl, cyclopentyl and cyclohexyl.

Groups containing two or more rings, such as biphenyl, phenoxypyridyl and benzylphenyl, which may be substituted, may be substituted on either ring unless otherwise specified herein.

Starting arylmethanesulfonyl fluoride compounds of formula II wherein Y is $SO_2F$ may be prepared, as shown in Flow Diagram I, by reacting an arylmethanebromide compound of the structural formula V with sodium sulfite to form a sodium arylmethanesulfonate compound of the structural formula VI, reacting the formula VI sulfonate compound with phosphorous pentachloride to form an arylmethanesulfonyl chloride compound of the structural formula VII, and reacting the sulfonyl chloride compound with potasium fluoride.

FLOW DIAGRAM I $Ar_1CH_2Br$ (V)

$\big\downarrow Na_2SO_3$ $Ar_1CH_2SO_2Na$ (VI)

$\big\downarrow PCl_5$

-continued

Ar₁CH₂SO₂Cl (VII)

↓ KF

Ar₁CH₂SO₂F

Starting arylmethanephosphonate compounds of formula II wherein Y is P(O) (OR₁)₂ may be prepared as shown in Flow Diagram II, by reacting an arylmethanebromide compound of the structural formula V with a tri-($C_1$–$C_4$alkyl) phosphite compound of the structural formula VIII.

FLOW DIAGRAM II

Ar₁CH₂Br (V)

↓ P(OR₁)₃
(VIII)

Ar₁CH₂P(O)(OR₁)₂

3-Aryl-2-fluoropropenal compounds of structural formula III may be prepared according to the procedures described in EP 811593-A1.

In order to facilitate a further understanding of this invention, the following examples are presented primarily for the purpose of illustrating more specific details thereof. The scope of the invention should not be deemed limited by the examples but encompasses the entire subject matter defined in the claims.

EXAMPLE 1

Preparation of (4-Fluoro-3-phenoxyphenyl)methane-sulfonyl Fluoride

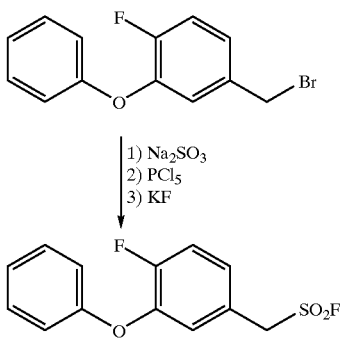

Step 1

A mixture of α-bromo-4-fluoro-3-phenoxytoluene (4.86 g, 17.3 mmol) and sodium sulfite (2.39 g, 19 mmol) in 50% aqueous methanol (20 ml) is heated at reflux for 5 hours and cooled to room temperature. The resultant colorless solid is collected by filtration and washed with chilled 50% aqueous methanol and methanol to obtain 3.4 g of sodium (4-fluoro-3-phenoxyphenyl)methanesulfonate. Another 1.8 g of product is recovered from the mother liquors.

Step 2

The sodium sulfonate obtained in step 1 is mixed with phosphorous pentachloride at room temperature for two days. An ice-water mixture is added and the aqueous solution is extracted with methylene chloride. The organic extract is washed with water, dried over anhydrous sodium sulfate, and concentrated in vacuo to obtain (4-fluoro-3-phenoxyphenyl)methanesulfonyl chloride as a syrup (2.05 g).

Step 3

The sulfonyl chloride obtained in step 2 (2.0 g, 6.65 mmol) is diluted with acetonitrile (20 ml). The resultant solution is treated with potassium fluoride (1.93 g, 33.25 mmol) and tetrabutylamonium fluoride (0.208 g, 0.66 mmol), stirred at room temperature for one day, poured into water, and extracted with ethyl acetate. The organic extract is washed with water, dried over anhydrous sodium sulfate, and concentrated in vacuo to obtain a residue. Flash chromatography of the residue on silica gel eluting with 15:85 ethyl acetate/hexanes gives (4-fluoro-3-phenoxyphenyl)methanesulfonyl fluoride (0.81 g, mp 59.5–61.5° C.) which is identified by $^1$H and $^{19}$F NMR spectral analyses.

EXAMPLE 2

Preparation of 1-(p-Chlorophenyl)-1-cyclopropyl-2-fluoro-4-(4-fluoro-3-phenoxyphenyl)-1,3-butadiene

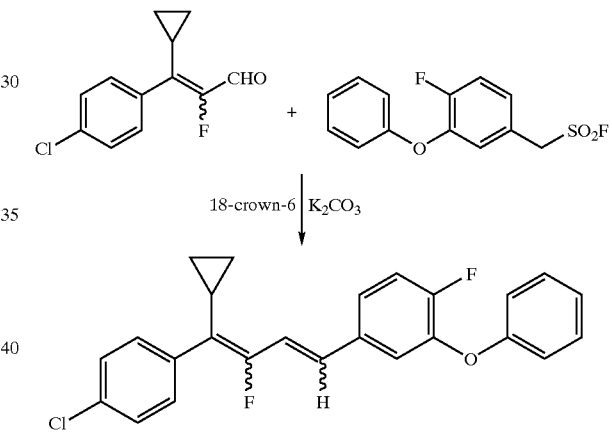

A mixture of p-chloro-β-cyclopropyl-α-fluoro-cinnamaldehyde (224.6 mg, 1 mmol), (4-fluoro-3-phenoxyphenyl)methanesulfonyl fluoride (312.7 mg, 1.1 mmol), potassium carbonate (552.8 mg, 4 mmol), and 18-crown-6 (13.2 mg, 0.05 mmol) in acetonitrile is stirred at room temperature overnight, quenched with water, and extracted with ethyl acetate. The organic extract is washed with water, dried over anhydrous sodium sulfate, and concentrated in vacuo to give the title product (380 mg, 94% pure by GC analysis, 93% yield) which is identified by $^1$H and $^{19}$F NMR spectral analyses.

EXAMPLE 3

Preparation of Diethyl (4-Fluoro-3-phenoxybenzyl)-phosphonate

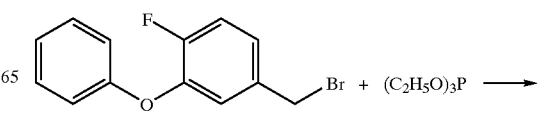

-continued

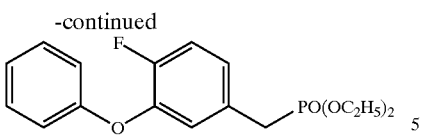

A mixture of 4-fluoro-3-phenoxybenzyl bromide (28.1 g, 100 mmol) and triethyl phosphite (18.27 g, 110 mmol) is heated at 90° C. for 30 minutes while allowing some low boiling materials to distill off. The resultant mixture is heated at 140° C. for 3.5 hours and distilled at 120° C./2 mmHg to give the title product as a syrup (32.1 g, 95% yield) which is identified by $^1$H and $^{19}$F NMR spectral analyses.

EXAMPLE 4

Preparation of 1-(p-Chlorophenyl)-1-cyclopropyl-2-fluoro-4-(4-fluoro-3-phenoxyphenyl)-1,3-butadiene

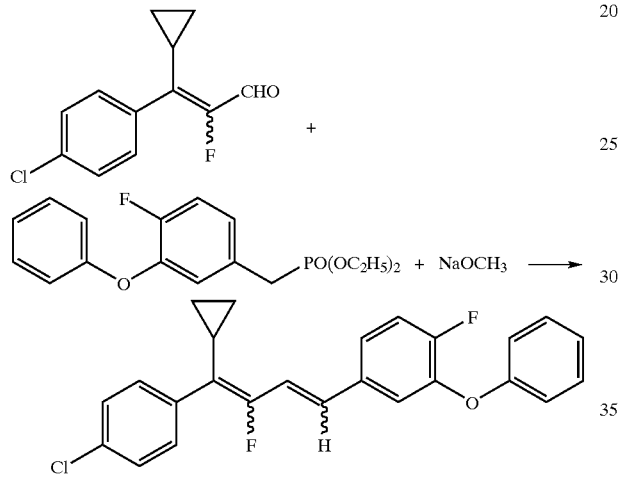

A stirred solution of diethyl (4-fluoro-3-phenoxybenzyl) phosphonate (2.64 g, 7.8 mmol) and p-chloro-β-cyclopropyl-α-fluorocinnamaldehyde (1.35 g, 6 mmol) in tetrahydrofuran (20 ml) is treated with sodium methoxide (562 mg, 9.36 mmol) at 0° C., stirred at room temperature overnight, quenched with 2 N aqueous hydrochloric acid, and extracted with ethyl acetate. The organic extract is washed sequentially with water, 2 N aqueous hydrochloric acid and water, dried over anhydrous sodium sulfate, and concentrated in vacuo to obtain a residue. Flash chromatography of the residue on silica gel eluting with 1:9 ethyl acetate/hexanes gives the title product as a syrup (2.15 g, 87.7% yield) which is identified by $^1$H and $^{19}$F NMR spectral analyses.

What is claimed is:

1. A process for the preparation of a 1,4-diaryl-2-fluoro-1,3-butadiene compound of the structural formula I

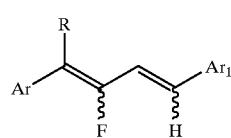

wherein

R is $C_1$–$C_4$-alkyl, $C_1$–$C_4$-haloalkyl, $C_3$–$C_6$-cycloalkyl or $C_3$–$C_6$-halocycloalkyl;

Ar is phenyl optionally substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups,
1- or 2-naphthyl optionally substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups; and $Ar_1$ is phenoxyphenyl optionally substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups,
phenyl optionally substituted with any combination of from one to five halogen, $C_1$–$C_4$-alkyl, $C_1$–$C_4$-haloalkyl, $C_1$–$C_4$-alkoxy, or $C_1$–$C_4$-haloalkoxy groups,
biphenyl optionally substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
benzylphenyl optionally substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
benzoylphenyl optionally substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups, or
1- or 2-naphthyl optionally substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, which process comprises reacting an arylmethanesulfonyl fluoride or arylmethanephosphonate compound of the structural formula II $$Ar_1CH_2Y \quad (II)$$

wherein Y is $SO_2F$ or $P(O)(OR_1)_2$, $R_1$ is $C_1$–$C_4$-alkyl, and $Ar_1$ is as described above with a 3-aryl-2-fluoropropenal compound of the structural formula III

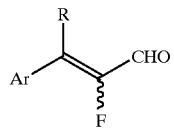

wherein R and Ar are as hereinbefore defined, in the presence of a base.

2. The process according to claim 1 wherein the base is selected from the group consisting of an alkali metal hydride, an alkali metal $C_1$–$C_6$-alkoxide, an alkali-metal hydroxide, an alkali metal carbonate, an alkaline earth metal hydroxide, an alkaline earth metal carbonate, a lithium base and a tri($C_1$–$C_6$-alkyl)amine.

3. The process according to claim 2 wherein the base is selected from the group consisting of an alkali metal $C_1$–$C_6$-alkoxide and an alkali metal carbonate.

4. The process according to claim 1 wherein the arylmethanesulfonyl fluoride or arylmethanephosphonate compound is reacted with the 3-aryl-2-fluoropropenal compound and the base in the presence of a solvent.

5. The process according to claim 4 wherein the solvent is selected from the group consisting of a carboxylic acid amide, an ether, a nitrile, a dialkyl sulfoxide, an aromatic hydrocarbon and a $C_1$–$C_6$-alcohol and mixtures thereof.

6. The process according to claim 5 wherein the solvent is selected from the group consisting of an ether and a nitrile.

7. The process according to claim 1 wherein the arylmethanesulfonyl fluoride or arylmethanephosphonate compound is reacted with the 3-aryl-2-fluoropropenal compound and the base at a temperature ranging from about −78° C. to 150° C.

8. The process according to claim 7 wherein the temperature range is from about −20° C. to 100° C.

9. The process according to claim 1 wherein

R is $C_1$–$C_4$-alkyl, $C_1$–$C_4$-haloalkyl, $C_3$–$C_6$-cycloalkyl or $C_3$–$C_6$-halocycloalkyl;

Ar is phenyl optionally substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups;

$Ar_1$ is 3-phenoxyphenyl optionally substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups, 3-biphenyl optionally substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups, or 3-benzylphenyl optionally substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups;

Y is $SO_2F$ or $P(O)(OR_2)_2$; and $R_1$ is $C_1$–$C_4$-alkyl.

10. The process according to claim 9 wherein

R is isopropyl or cyclopropyl;

Ar is phenyl optionally substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups;

$Ar_1$ is 3-phenoxyphenyl optionally substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups;

Y is $SO_2F$ or $P(O)(OR_1)_2$; and $R_1$ is $C_1$–$C_4$-alkyl.

11. The process according to claim 1 for the preparation of 1-(p-chlorophenyl)-1-cyclopropyl-2-fluoro-4-(4-fluoro-3-phenoxyphenyl)-1,3-butadiene.

12. The process according to claim 1 wherein Y is $SO_2F$.

13. The process according to claim 1 wherein Y is $P(O)(OR_1)_2$.

14. The process according to claim 13 wherein $R_1$ is ethyl.

15. The process according to claim 1 which further comprises a catalytically effective amount of a phase transfer catalyst.

* * * * *